(12) United States Patent
Shimada

(10) Patent No.: US 10,406,038 B2
(45) Date of Patent: Sep. 10, 2019

(54) DISPOSABLE DIAPER FOLDING METHOD AND FOLDING DEVICE

(71) Applicant: ZUIKO CORPORATION, Settsu-shi, Osaka (JP)

(72) Inventor: Takahiro Shimada, Osaka (JP)

(73) Assignee: Zuiko Corporation (JP)

( * ) Notice: Subject to any disclaimer, the term of this patent is extended or adjusted under 35 U.S.C. 154(b) by 637 days.

(21) Appl. No.: 14/654,712

(22) PCT Filed: Dec. 19, 2013

(86) PCT No.: PCT/JP2013/007472
§ 371 (c)(1),
(2) Date: Jun. 22, 2015

(87) PCT Pub. No.: WO2014/103259
PCT Pub. Date: Jul. 3, 2014

(65) Prior Publication Data
US 2016/0193088 A1 Jul. 7, 2016

(30) Foreign Application Priority Data

Dec. 26, 2012 (JP) .................. 2012-282640

(51) Int. Cl.
*A61F 13/15* (2006.01)
*A61F 13/496* (2006.01)

(52) U.S. Cl.
CPC .. *A61F 13/15747* (2013.01); *A61F 13/15764* (2013.01); *A61F 13/496* (2013.01)

(58) Field of Classification Search
CPC .............. A61F 13/15747; A61F 13/496; A61F 13/15764; A61F 13/15707
See application file for complete search history.

(56) References Cited

U.S. PATENT DOCUMENTS

| 5,868,727 A | 2/1999 | Barr et al. |
| 2003/0062121 A1* | 4/2003 | Franklin ........... A61F 13/15747 156/285 |

(Continued)

FOREIGN PATENT DOCUMENTS

| CN | 1415277 A | 5/2003 |
| CN | 1254269 A | 6/2005 |

(Continued)

OTHER PUBLICATIONS

Chinese Office Action dated Mar. 9, 2017.
International Search Report dated Feb. 18, 2014.
European Search Report dated Jun. 8, 2016.

*Primary Examiner* — Thanh K Truong
*Assistant Examiner* — Thomas M Wittenschlaeger
(74) *Attorney, Agent, or Firm* — Gerald E. Hespos; Michael J. Porco; Matthew T. Hespos

(57) ABSTRACT

The front part and the rear part of a diaper main body are each attracted by a first belt and a second belt arranged so as to separate from each other as the first belt and the second belt move to the downstream side of the conveying path. The diaper main body is attracted by the first belt only in a range other than a non-attracting range thereof covering from a crease to a prescribed position in a longitudinal direction. When the respective belts are moved, the front part and the rear part of the diaper main body are separated from each other in a state in which the diaper main body separates from the first belt in the non-attracting range. Then, respective side panels are folded inward between the front part and the rear part of the diaper main body that separate from each other.

12 Claims, 7 Drawing Sheets

(56) References Cited

U.S. PATENT DOCUMENTS

| | | |
|---|---|---|
| 2003/0084767 A1 | 5/2003 | Tanaka et al. |
| 2003/0221767 A1* | 12/2003 | Vogt ................. A61F 13/15747 156/160 |
| 2004/0112527 A1* | 6/2004 | Keene ................ B65H 19/1852 156/304.1 |
| 2010/0168708 A1* | 7/2010 | Umebayashi ..... A61F 13/15747 604/385.03 |
| 2011/0247747 A1* | 10/2011 | Schneider ......... A61F 13/15747 156/216 |
| 2011/0287919 A1 | 11/2011 | Umebayashi |
| 2012/0324633 A1 | 12/2012 | Back |
| 2013/0059713 A1 | 3/2013 | Nakano |
| 2013/0303354 A1 | 11/2013 | Sablone |
| 2014/0303587 A1 | 10/2014 | Back |

FOREIGN PATENT DOCUMENTS

| | | |
|---|---|---|
| CN | 102264329 A | 11/2011 |
| JP | 09-000567 | 1/1997 |
| JP | 9-131364 | 5/1997 |
| JP | 2011-200568 | 10/2011 |
| WO | 2011101018 A1 | 8/2011 |
| WO | 2011/126743 | 10/2011 |
| WO | 2012085698 A1 | 6/2012 |

* cited by examiner

DISPOSABLE DIAPER FOLDING METHOD AND FOLDING DEVICE

TECHNICAL FIELD

The present invention relates to a method and a device for folding disposable diapers.

BACKGROUND ART

Conventionally, a known disposable diaper has a main body portion that extends from a front belly part to a back part via a crotch part and a pair of side portions through which the front part and the rear part of the main body portion folded in half are joined together to cover the side surfaces of the lumber part of a wearer when the disposable diaper is worn.

The disposable diaper expands in its width direction in a state in which the respective side portions protrude from the main body portion to its both sides. Therefore, the respective side portions are folded inward between the front part and the rear part of the main body portion, whereby the disposable diaper is put in a compact form for shipping (for example, Japanese Unexamined Patent Publication No. H9-131364).

A folding device described in Japanese Unexamined Patent Publication No. H9-131364 has two conveying belts that convey a disposable diaper while sandwiching the same from its both front and rear sides and folding means for folding respective side portions inward between the front part and the rear part of a main body portion.

The respective conveying belts are arranged so as to separate from each other toward a downstream side in the conveying direction of each disposable diaper and convey the disposable diaper with its waist opening directed to the downstream side in the conveying direction. In addition, one of the conveying belts conveys the disposable diaper with the front part of the main body portion attached thereto. The other of the conveying belts conveys the disposable diaper with the rear part of the main body portion attached thereto.

Accordingly, the front part and the rear part of the main body portion separate from each other so as to widen the waist opening as the disposable diaper is conveyed by the respective conveying belts. When such a state is established and the folding means comes in contact with the respective side portions of the disposable diaper and the respective side portions and the folding means are displaced relative to each other with the conveyance of the disposable diaper, the respective side portions are folded inward between the front part and the rear part of the main body portion.

However, the folding device described in Japanese Unexamined Patent Publication No. H9-131364 conveys the disposable diaper with the waist opening directed to the downstream side in the conveying direction. Therefore, if the disposable diaper keeps conveying in the conveying direction of the folding device in this state, the edge portion of the waist opening gets stuck on the opening portion of a packaging bag when the folded disposable diaper is packaged (for example, the disposable diaper is put in the packaging bag). As a result, the disposable diaper cannot be efficiently packaged.

SUMMARY OF INVENTION

It is an object of the present invention to provide a disposable diaper folding method and a folding device capable of folding respective side portions inward between the front part and the rear part of a main body portion while conveying a disposable diaper in a direction in which the disposable diaper is easily packaged.

In order to solve the above problem, the inventors of the present application have employed a method for folding respective side portions inward between the front part and the rear part of a main body portion while conveying a disposable diaper with the crease of the main body portion directed to a downstream side. However, when the crease of the main body portion is directed to the downstream side, the front part and the rear part of the main body portion are constrained to each other by the crease on the distal end side thereof. Therefore, the front part and the rear part cannot be separated from each other only by holding the entire front part and the entire rear part of the main body portion with two conveying belts and separating the conveying belts from each other. To this end, the inventors of the present application have conceived the following inventions in which the position(s) of the front part and/or the rear part of a main body portion attracted by respective conveying belts is/are adjusted to allow the separation between the front part and the rear part of the main body portion with the crease of the main body portion directed to a downstream side.

Specifically, the present invention provides a disposable diaper folding method for a disposable diaper having a main body portion that extends from a front belly part to a back part via a crotch part of a wearer when the disposable diaper is worn and a pair of side portions that joins together a front part and a rear part of the main body portion folded in half based on a crease, the method comprising: a separating step of moving a first belt and a second belt in a state in which the front part of the main body portion is attracted by one of the first belt and the second belt and the rear part of the main body portion is attracted by the other of the first belt and the second belt and separating the front part and the rear part of the main body portion from each other while conveying the disposable diaper along a predetermined conveying path by a movement of the first belt and the second belt, the first belt and the second belt being arranged so as to face each other across the conveying path for the disposable diaper and separate from each other as the first belt and the second belt move to a downstream side of the conveying path; and a folding step of folding the respective side portions inward between the front part and the rear part of the main body portion, which are separated from each other, wherein the separating step conveys the disposable diaper along the conveying path such that the crease is directed to the downstream side in a state in which the main body portion is attracted by at least one of the first belt and the second belt only in a range other than a non-attracting range thereof covering from the crease to a predetermined position in a longitudinal direction, thereby separating the front part and the rear part of the main body portion from each other while separating the main body portion from at least the one belt in the non-attracting range.

In addition, the present invention provides a disposable diaper folding device for a disposable diaper having a main body portion that extends from a front belly part to a back part via a crotch part of a wearer when the disposable diaper is worn and a pair of side portions that joins together a front part and a rear part of the main body portion folded in half based on a crease, the device comprising: a first conveying unit that has a first belt and a first moving mechanism configured to move the first belt in a state in which one of the front part and the rear part of the main body portion is attracted by the first belt; a second conveying unit that has a second belt arranged so as to face the first belt across a predetermined conveying path and separate from the first belt as the second belt moves to a downstream side of the conveying path and that has a second moving mechanism configured to move the second belt in a state in which the other of the front part and the rear part of the main body portion is attracted by the second belt such that the front part and the rear part of the main body portion separate from each other while conveying the disposable diaper along the conveying path in cooperation with the first belt; and a folding unit that folds the respective side portions inward between the front part and the rear part of the main body portion, the front part and the rear part being separated from each other by the first conveying unit and the second conveying unit, wherein at least one of the first belt and the second belt has a plurality of limited attracting regions for attracting the main body portion only in a range other than a non-attracting range thereof covering from the crease to a predetermined position in a longitudinal direction, and the first conveying unit and the second conveying unit convey the disposable diaper along the conveying path such that the crease is directed to the downstream side in a state in which the main body portion is attracted to the limited attracting region only in the range other than the non-attracting range thereof, thereby separating the front part and the rear part of the main body portion from each other while separating the main body portion from at least the one belt in the non-attracting range.

According to the present invention, it is possible to fold respective side portions between the front part and the rear part of a main body portion while conveying a disposable diaper in a direction in which the disposable diaper is easily packaged.

DESCRIPTION OF EMBODIMENTS

Hereinafter, a description will be given of an embodiment of the present invention with reference to the accompanying drawings. Note that the following embodiment is a materialized example of the present invention but does not limit the technical scope of the present invention.

Figure 1:
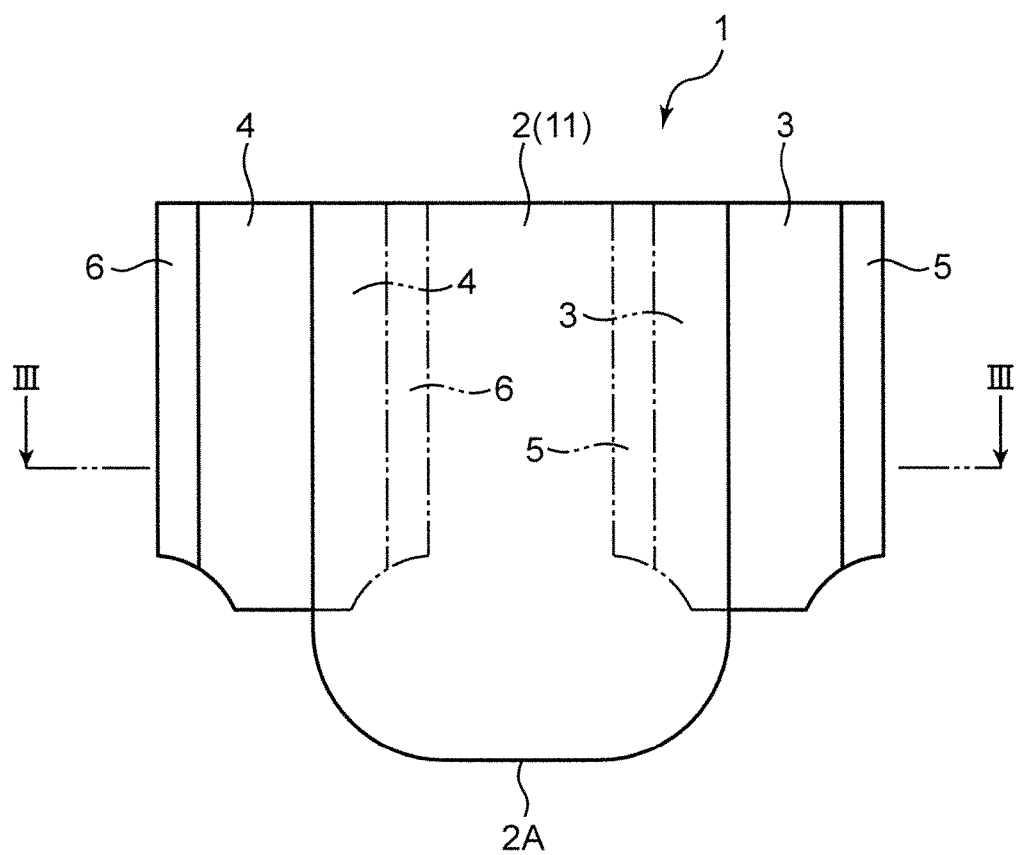
FIG. 1 is a front view showing a disposable diaper according to an embodiment of the present invention.
Figure 2:
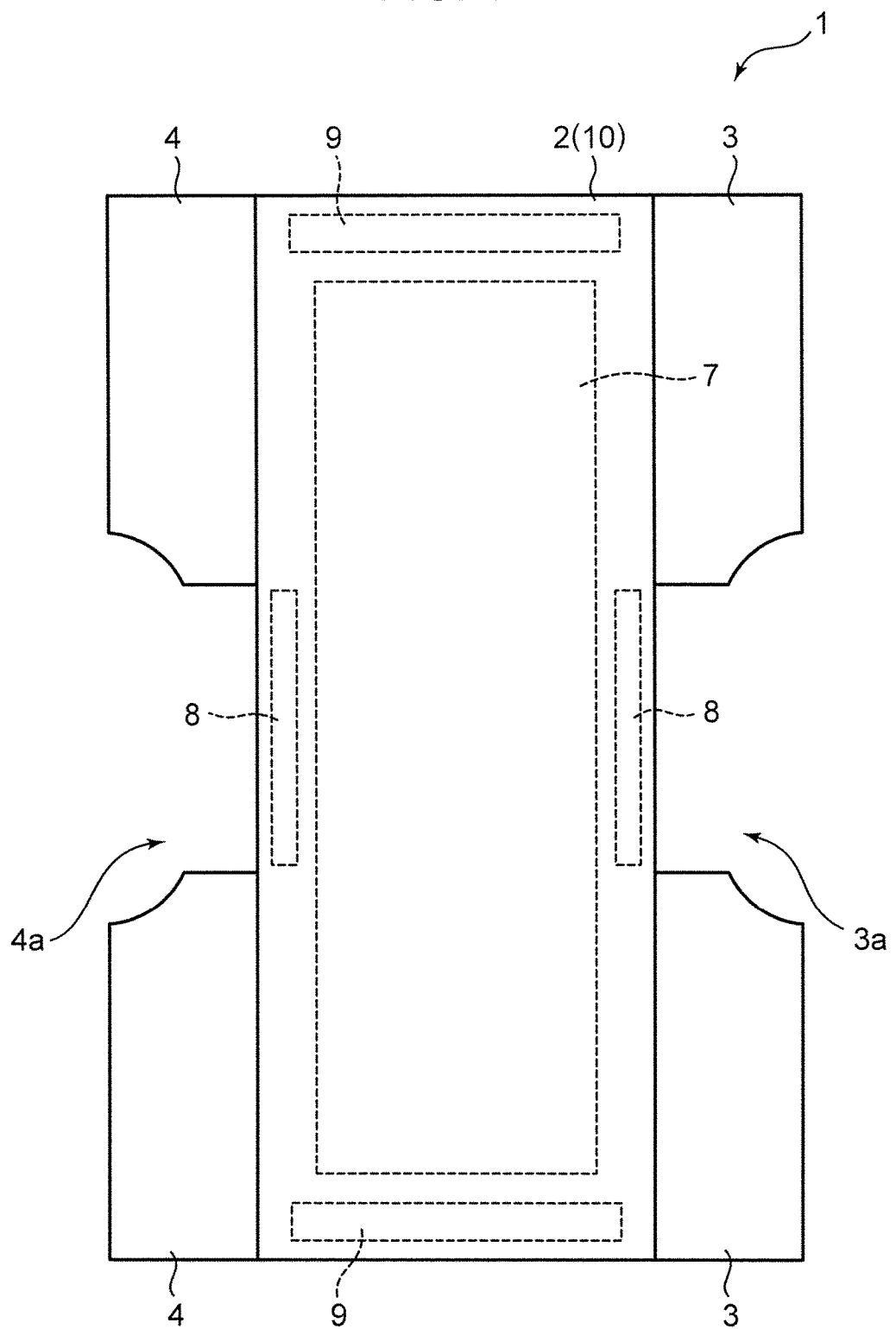
FIG. 2 is a plan view showing the side seal portions of the disposable diaper in FIG. 1 in their spread fashion.

With reference to FIGS. 1 and 2, a disposable diaper 1 is a so-called underpants-shaped diaper. Specifically, the disposable diaper 1 has a diaper main body (main body portion) 2 that extends from the front belly part to the back part via the crotch part of a wearer when the disposable diaper 1 is worn and four side panel pieces (side pieces) 3 and 4, each of which protrudes from both ends in the longitudinal direction (vertical direction in FIG. 2) of the diaper main body 2 to the width direction (horizontal direction in FIG. 2) of the diaper main body 2. The disposable diaper 1 is formed in an underpants shape when the respective side panel pieces 3 are bonded to each other through their side seal portions 5 and the respective side panel pieces 4 are bonded to each other through their side seal portions 6 in a state in which the diaper main body 2 is folded in half based on a crease (crotch part) 2A. As a result, the respective side panel pieces 3 bonded to each other through the side seal portions 5 and the respective side panel pieces 4 bonded to each other through the side seal portions 6 constitute a pair of side portions that covers the side surfaces of the lumbar part of a wearer.

Hereinafter, a description will be given of the specific configuration of the disposable diaper 1 with reference to FIGS. 1 to 3.

The diaper main body 2 is capable of absorbing body wastes (for example, urine) of a wearer and has elasticity at its appropriate portions. Specifically, the diaper main body 2 has an absorber 7 capable of absorbing body wastes of a wearer, elastic members 8 for legs provided at positions corresponding to the crotch part of the wearer, a pair of elastic members 9 for waist provided at positions corresponding to the front belly part and the back part of the wearer, and inner and outer sheets 10 and 11 that sandwich the absorber 7, the elastic members 8 for legs, and the elastic members 9 for waist between them.

The inner sheet 10 is a substantially rectangular sheet that is directed to the body surface side of a wearer when the disposable diaper 1 is worn and has liquid permeability. The inner sheet 10 can be constituted by, for example, a nonwoven sheet and/or a mesh sheet having liquid permeability.

The outer sheet 11 is a sheet that is directed to the outer side of a wearer when the disposable diaper 1 is worn and has liquid impermeability. The outer sheet 11 can be constituted by a polyethylene film or a nonwoven fabric having water repellency and air permeability. In addition, the outer sheet 11 is a substantially rectangular sheet having a size equivalent to that of the inner sheet 10.

The absorber 7 absorbs liquid that passes through the inner sheet 10. Specifically, the absorber 7 is molded in such a way as to stack crashed pulps or materials in which crashed pulps and highly water-absorptive polymers are mixed together. In addition, the absorber 7 has a substantially rectangular shape or a hourglass shape having a longitudinal size smaller than those of the respective sheets 10 and 11 and a width size narrower than those of the respective sheets 10 and 11. The absorber 7 is arranged between the sheets 10 and 11 such that vacant areas exist at both end portions in the longitudinal direction of the respective sheets 10 and 11 and at both end portions in the width direction (horizontal direction) of the respective sheets 10 and 11. Further, as shown in FIG. 3, the absorber 7 is bonded to the sheets 10 and 11 in a state of being sandwiched between the inner sheet 10 and the outer sheet 11.

The respective elastic members 8 for legs are such that the diaper main body 2 is raised and brought into intimate contact with the crotch part of a wearer when the disposable diaper 1 is worn to prevent body wastes from leaking from the gap between the diaper main body 2 and the body surface of the wearer. At least parts of the respective elastic members 8 for legs are provided at positions on both outer sides in the width direction of the absorber 7 and at positions between the respective side panel pieces 3 and between the respective side panel pieces 4. In addition, the respective elastic members 8 for legs are attached on the diaper main body 2 in their expanding state in the longitudinal direction of the diaper main body 2. As not shown, the respective elastic members 8 for legs are bonded to the sheets 10 and 11 in a state of being sandwiched between the inner sheet 10 and the outer sheet 11. The respective elastic members 8 for legs can be constituted by polyurethane, natural rubber, or sheets or threads made of a thermoplastic resin.

The respective elastic members 9 for waist are such that the diaper main body 2 is fastened to the front belly part or the back part of a wearer when the disposable diaper 1 is worn to prevent the disposable diaper 1 from being pulled down. The respective elastic members 9 for waist are attached on the diaper main body 2 under a stretched state in the width direction of the absorber 7. As not shown, the respective elastic members 9 for waist are bonded to the sheets 10 and 11 in a state of being sandwiched between the inner sheet 10 and the outer sheet 11. The respective elastic members 9 for waist can be constituted by polyurethane, natural rubber, or sheets or threads made of a thermoplastic resin.

The respective side panel pieces 3 extend from both end portions in the longitudinal direction (front and rear direction) of the diaper main body 2 to one side in the horizontal direction (right side in FIGS. 1 and 2) and has elasticity in the horizontal direction. A gap portion 3a is formed between the respective side panel pieces 3 and used as a leg hole when the right edge portions of the respective side panel pieces 3 are bonded to each other through the side seal portions 5. As shown in FIG. 3, the respective side panel pieces 3 are bonded to the sheets 10 and 11 in a state of being sandwiched between the inner sheet 10 and the outer sheet 11 on the right side of the absorber 7.

In addition, the respective side panel pieces 3 are sheets made of a thermoplastic material. Specifically, the respective side panel pieces 3 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

The respective side panel pieces 4 extend from both end portions in the longitudinal direction of the diaper main body 2 to one side in the horizontal direction (left side in FIGS. 1 and 2) and has elasticity in the horizontal direction. A gap portion 4a is formed between the respective side panel pieces 4 and used as a leg hole when the left edge portions of the respective side panel pieces 4 are bonded to each other through the side seal portions 6. As shown in FIG. 3, the respective side panel pieces 4 are bonded to the sheets 10 and 11 in a state of being sandwiched between the inner sheet 10 and the outer sheet 11 on the left side of the absorber 7.

In addition, the respective side panel pieces 4 are sheets made of a thermoplastic material. Specifically, the respective side panel pieces 4 can be constituted by an elastic film, an elastic nonwoven fabric, a laminated body of an elastic film and a nonwoven fabric, or a laminated body of thread rubber and a nonwoven fabric each of which is made of one or at least two of the materials of a block copolymer of polystyrene, a block copolymer of polyisoprene, a block copolymer of polybutadiene, a copolymer of ethylene, natural rubber, and urethane.

Figure 3:
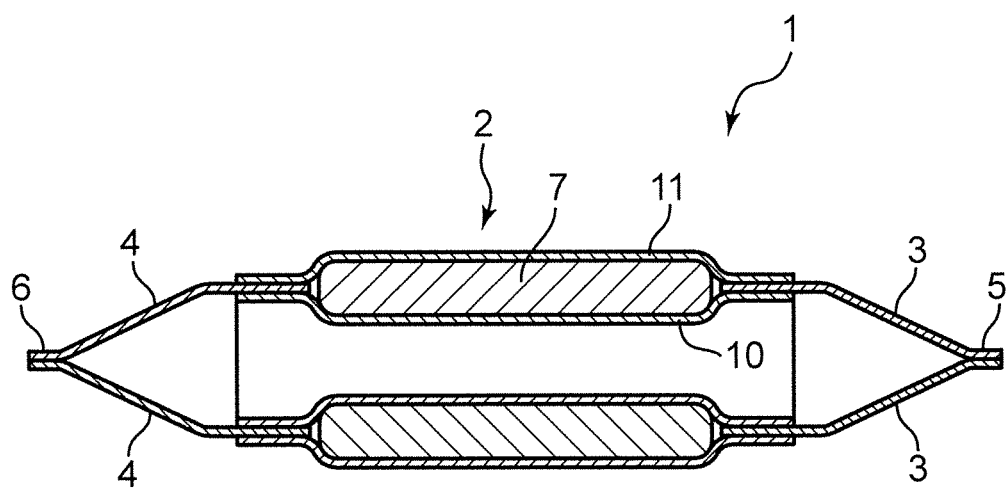
FIG. 3 is a cross-sectional view taken along line III-III in FIG. 1.
Figure 4:
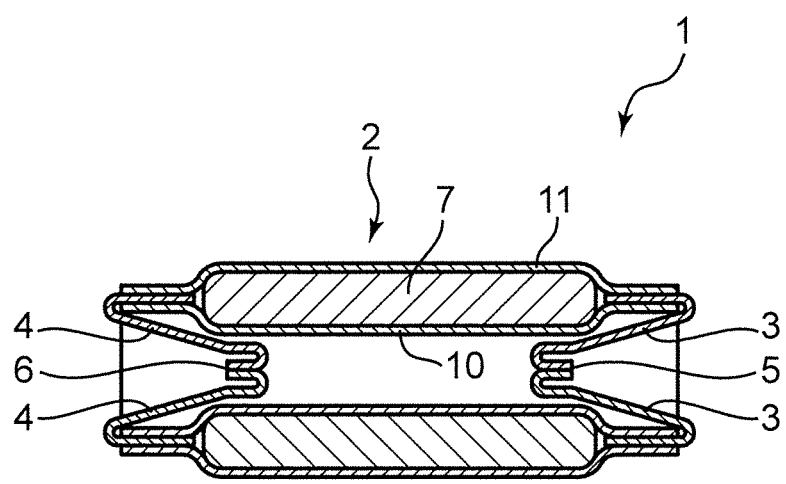
FIG. 4 is a view corresponding to FIG. 3, showing a state in which respective side portions are folded inward between the front part and the rear part of a diaper main body.

As shown in FIG. 3, the disposable diaper 1 expands in the width direction (horizontal direction) in a state in which the respective side panel pieces 3 and 4 protrude toward both sides of the diaper main body 2. Therefore, as shown in FIG. 4, the respective side panel pieces 3 and 4 are folded inward between the front part and the rear part of the diaper main body 2 folded in half based on the crease 2A (see FIG. 1), whereby the disposable diaper 1 can be put in a compact form for shipping.

Hereinafter, a description will be given, with reference to FIG. 5, of a folding device 14 for folding the disposable diaper 1 so as to transform from a state shown in FIG. 3 to a state shown in FIG. 4.

The folding device 14 has a first conveying unit 15, a second conveying unit 16, and a third conveying unit 17 for conveying the disposable diaper 1 along a predetermined conveying path R1, a folding unit 18 for folding the respective side panel pieces 3 and 4 inward between the front part and the rear part of the diaper main body 2, and a controller 19 that controls the driving of the respective conveying units 15 to 17 and the folding unit 18.

The first conveying unit 15 has a first belt 20 for attracting the front part or the rear part of the diaper main body 2, a plurality of rollers (first moving mechanism) 21 to 23 for circulating the first belt 20 along a predetermined path, a first conveying motor (first moving mechanism) 24 that rotates and drives the driving roller 23 among the respective rollers 21 to 23, a first suctioning section 25 for imparting an attracting force to the first belt 20, and a first sensor (first detector) 26 for detecting marks 20d of the first belt 20 that will be described later.

The first belt 20 is bridged between the respective rollers 21 and 22 to be arranged in parallel with the conveying path R1 and circulates along the predetermined path with the rotation of the driving roller 23.

Figure 6:
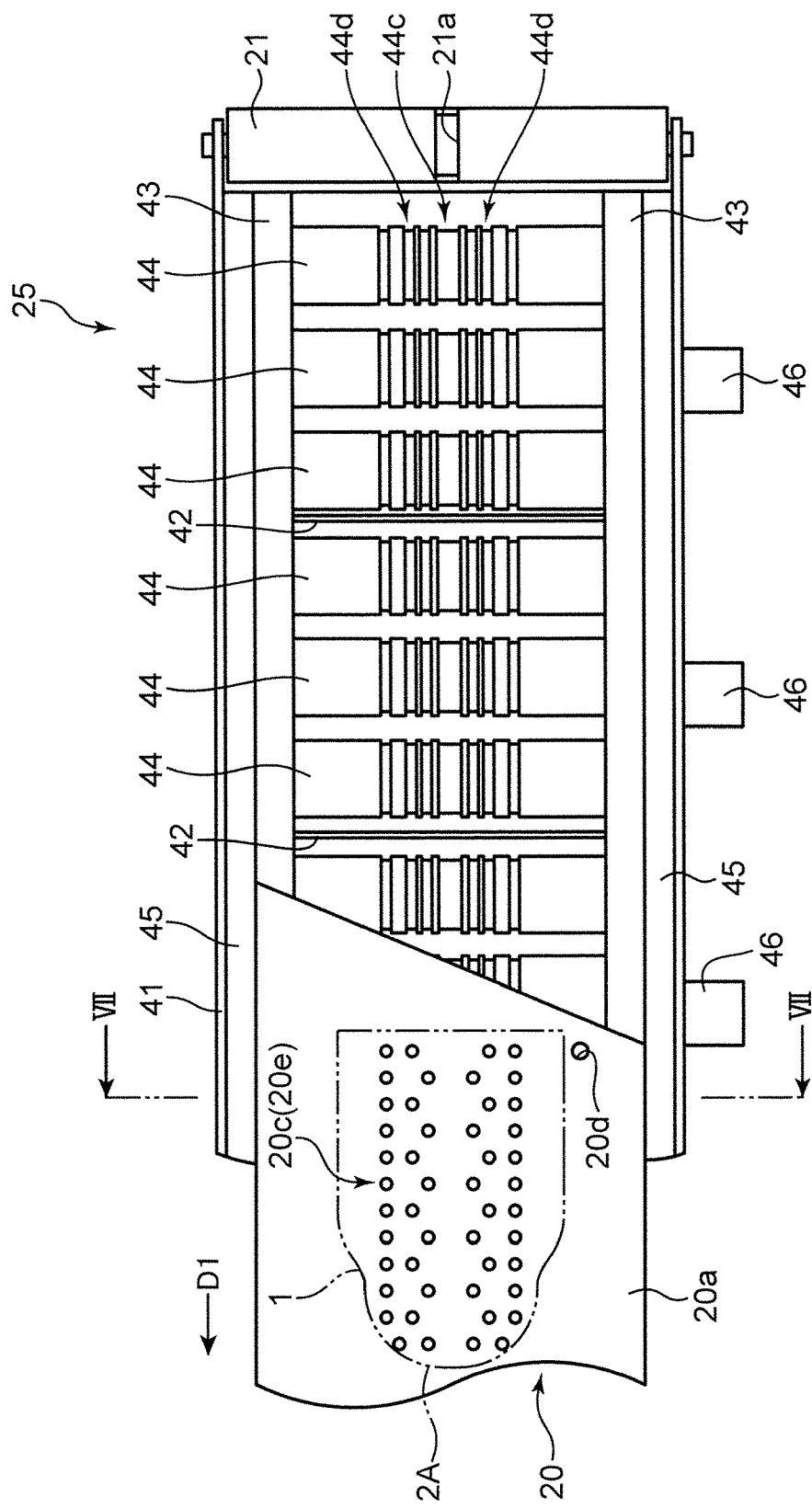
FIG. 6 is a bottom view showing a part of a first conveying unit in FIG. 5.
Figure 7:
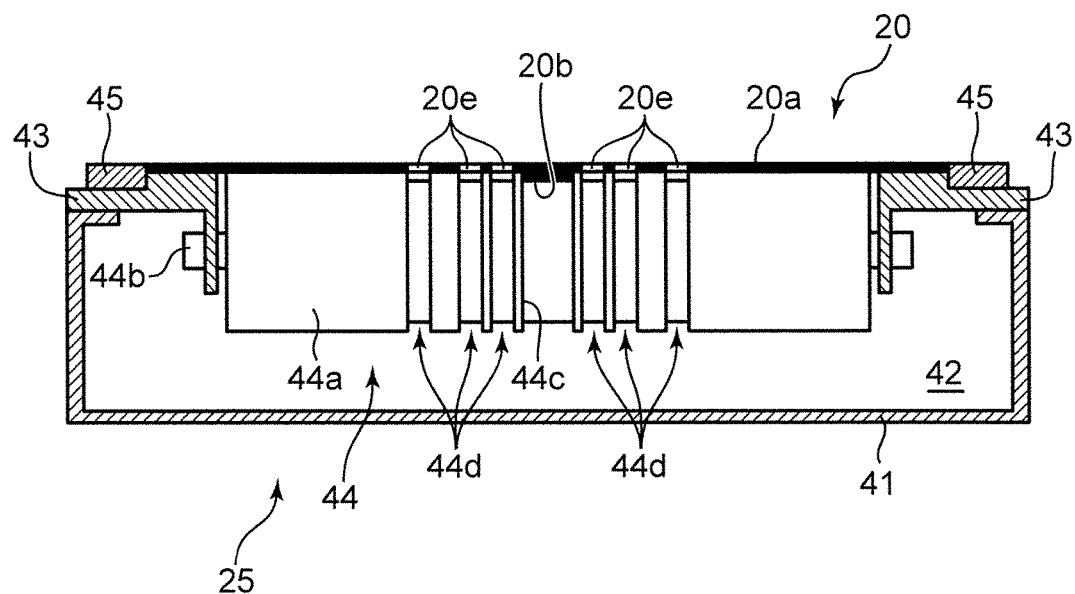
FIG. 7 is a cross-sectional view taken along line VII-VII in FIG. 6.

In addition, as shown in FIGS. 6 and 7, the first belt 20 has a belt main body 20a, a guiding protrusion 20b (see FIG. 7) formed on the rear surface of the belt main body 20a along the longitudinal direction of the belt main body 20a, a plurality of restricted attracting regions 20c (only one shown in FIG. 6) provided in the belt main body 20a to attract the diaper main body 2, and the marks 20d that indicate the positions of the respective restricted attracting regions 20c on the belt main body 20a.

The guiding protrusion 20b engages with engagement grooves 21a (only one shown in FIG. 6 for the roller 21) formed in the respective rollers 21 to 23 to prevent the movement of the first belt 20 in a direction orthogonal to the conveying path R1 with respect to the respective rollers 21 to 23. Further, a portion of the rear surface of the belt main body 20a other than the guiding protrusion 20b is formed to be flat (see FIG. 7). Thus, the first belt 20 is formed by a flat belt that receives power from the driving roller 23 without using a gear.

As shown in FIG. 6, each of the restricted attracting regions 20c is restricted in a range corresponding to the size of the front part or the rear part of one diaper main body 2. Specifically, as shown in FIGS. 6 and 7, each of the restricted attracting regions 20c according to the embodiment is defined as a region in which a plurality of penetrating holes 20e that penetrate from the front side to the rear side of the belt main body 20a is formed. Note that FIG. 6 shows the disposable diaper 1 with the respective side panels 3 and 4 shrinking due to their elasticity (the respective side panels 3 and 4 shown in FIG. 6 are smaller in size than those shown in FIGS. 1 and 2).

The respective marks 20d are provided in the vicinity of the respective restricted attracting regions 20c in the belt main body 20a. In addition, the marks 20d are constituted by holes that penetrate from the front side to the rear side of the belt main body 20a. The positions of the marks 20d are detected by the first sensor 26 that will be described later.

Figure 5:
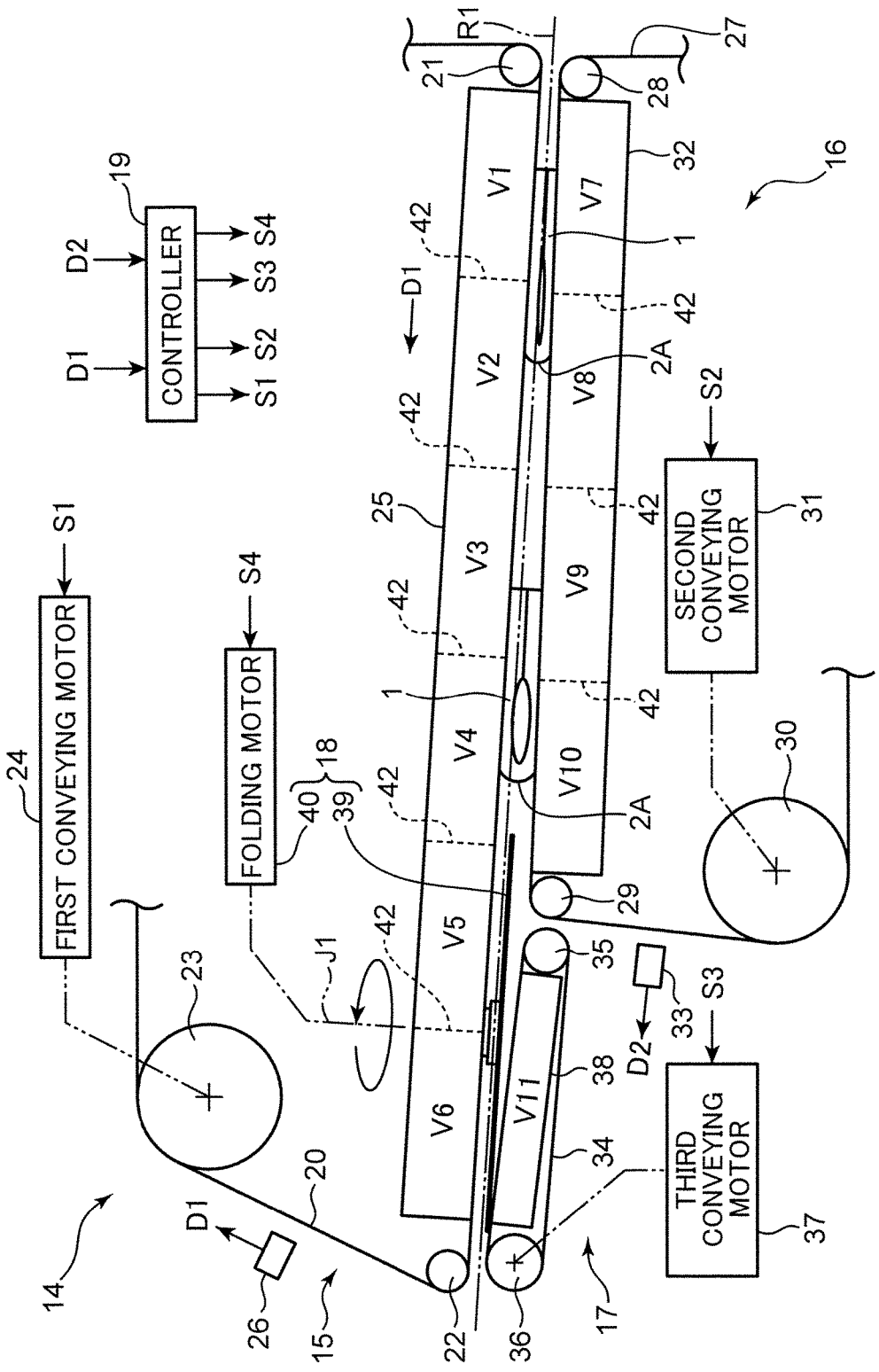
FIG. 5 is a side view schematically showing the entire configuration of a folding device according to the embodiment of the present invention.

With reference to FIGS. 5 to 7, the first suctioning section 25 is provided along the conveying path R1 on the rear surface side (the upper side in FIG. 5) of the first belt 20 and imparts an attracting force to a part of the first belt 20 that faces the conveying path R1. Specifically, the first suctioning section 25 has first suctioning chambers V1 to V6 set at negative pressure and slidingly contacts the first belt 20 such that the respective restricted attracting regions 20c successively face the first suctioning chambers V1 to V6.

The first suctioning section 25 has a substantially-rectangular box-shaped member 41 that is opened toward the first belt 20 and extends along the conveying path R1, five partitioning plates 42 that partition space inside the box-shaped member 41 into the six first suctioning chambers V1 to V6 arranged side by side along the conveying path R1, a pair of angles 43 that is provided at the opening end of the box-shaped member 41 and extends along the conveying path R1, a plurality of supporting rollers 44 provided between the respective angles 43, a pair of guiding pieces 45 fixed to the respective angles 43, and six ducts 46 (only three shown in FIG. 6) for discharging air inside the respective first suctioning chambers V1 to V6. Pressure (negative pressure) inside the respective suctioning chambers V1 to V6 is separately adjustable according to the discharging amount of air from the respective ducts 46.

The respective supporting rollers 44 are arranged so as to traverse the opening of the box-shaped member 41 in a state of being rotatable with respect to the box-shaped member 41 and support the first belt 20 from its rear side. In the embodiment, the supporting rollers 44 are provided in units of three for each of the first suctioning chambers V1 to V6.

Specifically, the respective supporting rollers 44 have a roller main body 44a provided between the respective angles 43 and a rotating shaft 44b rotatably supporting the roller main body 44a with respect to the angles 43. The roller main body 44a has a guiding groove 44c and six rows of ventilation grooves 44d over its entire periphery. The engagement groove 44c engages with the guiding protrusion 20b of the first belt 20 to restrict the movement of the first belt 20 in the direction orthogonal to the conveying path R1 with respect to the roller main body 44a. In addition, the ventilation grooves 44d are provided at positions over which the respective penetrating holes 20e of the first belt 20 pass through and used to reliably supply negative pressure inside the first suctioning chambers V1 to V6 to the penetrating holes 20e even in a state in which the first belt 20 is brought into intimate contact with the peripheral surface of the roller main body 44a.

The respective guiding pieces 45 restrict the movement of the first belt 20 supported by the respective supporting rollers 44 in the direction orthogonal to the conveying path R1.

With reference to FIG. 5, the first sensor 26 detects, on the downstream side of the roller 22, whether the marks 20d of the first belt 20 have passed through. Then, the first sensor 26 outputs its detection signal D1 to the controller 19 that will be described later.

Hereinafter, a description will be given of the second conveying unit 16 that is used to separate the front part and the rear part of the diaper main body 2 from each other while conveying the disposable diaper 1 along the conveying path R1 in cooperation with the first conveying unit 15 described above.

The second conveying unit 16 has a second belt 27 for attracting the front part or the rear part of the diaper main body 2, a plurality of rollers (second moving mechanism) 28 to 30 for circulating the second belt 27 along a predetermined path, a second conveying motor (second moving mechanism) 31 that rotates and drives the driving roller 30 among the respective rollers 28 to 30, a second suctioning section 32 for imparting an attracting force to the second belt 27, and a second sensor (second detector) 33 for detecting marks 27d of the second belt 27 that will be described later.

The second belt 27 is bridged between the respective rollers 28 and 29 to face the first belt 20 across the conveying path R1 and arranged so as to separate from the first belt 20 as the second belt 27 moves to the downstream side of the conveying path R1. In addition, the second belt 27 circulates along the predetermined path with the rotation of the driving roller 30.

Figure 8:
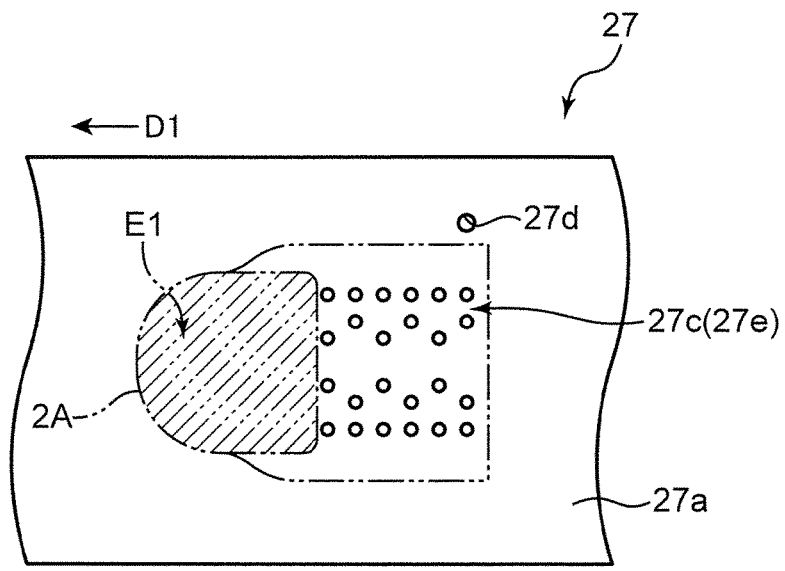
FIG. 8 is a plan view showing a part of the second belt of a second conveying unit in FIG. 5 in its enlarged fashion.

In addition, as shown in FIG. 8, the second belt 27 has a belt main body 27a, a plurality of limited attracting regions 27c (only one shown in FIG. 8) provided in the belt main body 27a to attract the diaper main body 2, and the marks 27d that indicate the positions of the respective limited attracting regions 27c on the belt main body 27a.

Note that although not shown in the figures, a guiding protrusion similar to the guiding protrusion 20b of the first belt 20 is provided on the rear surface of the belt main body 27a and engagement grooves that engage with the guiding protrusion are provided in the respective rollers 28 to 30. In addition, a portion of the rear surface of the belt main body 27a other than the guiding protrusion is formed to be flat. That is, the second belt 27 is also formed by a flat belt like the first belt 20.

Like the restricted attracting regions 20c, each of the limited attracting regions 27c is restricted in a range corresponding to the size of the front part or the rear part of one diaper main body 2. In addition, the limited attracting region 27c is limited to a range narrower than the restricted attracting region 20c. Specifically, the limited attracting region 27c is set so as to attract the diaper main body 2 only in a range other than a non-attracting range E1 thereof covering from the crease 2A to a predetermined position in the longitudinal direction.

With reference to FIG. 5, the second suctioning section 32 is provided along the conveying path R1 on the rear surface side (the lower side in FIG. 5) of the second belt 27 and imparts an attracting force to a part of the second belt 27 that faces the conveying path R1. Specifically, the second suctioning section 32 has second suctioning chambers V7 to V10 set at negative pressure and slidingly contacts the second belt 27 such that the respective limited attracting regions 27c successively face the second suctioning chambers V7 to V10. Note that since the second suctioning section 32 has configurations similar to those of the first suctioning section 25 in regard to other points, their descriptions will be omitted.

The second sensor 33 detects, on the downstream side of the roller 29, whether the marks 27d of the second belt 27 have passed through. Then, the second sensor 33 outputs its detection signal D2 to the controller 19 that will be described later.

Hereinafter, a description will be given of the third conveying unit 17 that is provided on the downstream side of the second conveying unit 16 so as to be capable of receiving the front part or the rear part of the diaper main body 2 attracted by the second belt 27 and makes the front part and the rear part of the diaper main body 2 come close to each other while conveying the disposable diaper 1 along the conveying path R1 in cooperation with the first conveying unit 15.

The third conveying unit 17 has a third belt 34 for attracting the front part or the rear part of the diaper main body 2, two rollers (third moving mechanism) 35 and 36 for circulating the third belt 34, a third conveying motor (third moving mechanism) 37 that rotates and drives the driving roller 36 among the respective rollers 35 and 36, and a third suctioning section (third moving mechanism) 38 for imparting an attracting force to the third belt.

The third belt 34 is bridged between the respective rollers 35 and 36 to face the extended portion of the first belt 20 across the conveying path R1 and come close to the first belt 20 as the third belt 34 moves to the downstream side of the conveying path R1, the extended portion extending to the downstream side of the second belt 27 on the conveying path R1. In addition, the third belt 34 circulates between the respective rollers 35 and 36 with the rotation of the driving roller 36.

Moreover, the third belt 34 has an attracting region (not shown) for attracting the front part or the rear part of the diaper main body 2 in a continuous fashion.

The third suctioning section 38 is provided along the conveying path R1 on the rear surface side (the lower side in FIG. 5) of the third belt 34 and imparts an attracting force to a part of the third belt 34 that faces the conveying path R1. Specifically, the third suctioning section 38 has a third suctioning chamber V11 set at negative pressure and slidingly contacts the third belt 34 such that the attracting region (not shown) provided in the third belt 34 faces the third suctioning section 38. Note that since the third suctioning section 38 has configurations similar to those of the first suctioning section 25 in regard to other points, their descriptions will be omitted.

Hereinafter, a description will be given, with reference to FIGS. 5, 9, and 10, of the folding unit 18 that folds the respective side panel pieces 3 and 4 inward between the front part and the rear part of the diaper main body 2.

The folding unit 18 is capable of folding the respective side panel pieces 3 and 4 inward between the front part and the rear part of the diaper main body 2 at the place between the first belt 20 and the third belt 34.

Specifically, the folding unit 18 has a pair of impellers 39 that is provided on both sides of the first belt 20 across the conveying path R1 and a pair of folding motors 40 (only one shown in FIG. 5) that rotates the respective impellers 39 about rotating shafts J1.

The impellers 39 have an impeller main body 39a and three blades 39b that protrude outward from the impeller main body 39a. The respective blades 39b are arranged at regular intervals (at an interval of 120° in the embodiment) about the rotating shaft J1 and have the same length. In addition, the respective blades 39b have a fan-shaped plane whose width becomes larger toward its distal end side. The distance between the respective rotating shafts J1 is set larger than twice the radius from the rotating shaft J1 to the peripheral margins of the blades 39b. Thus, the contact between the blades 39b of the respective impellers 39 is avoided regardless of the rotating positions of the respective impellers 39.

Figure 9:
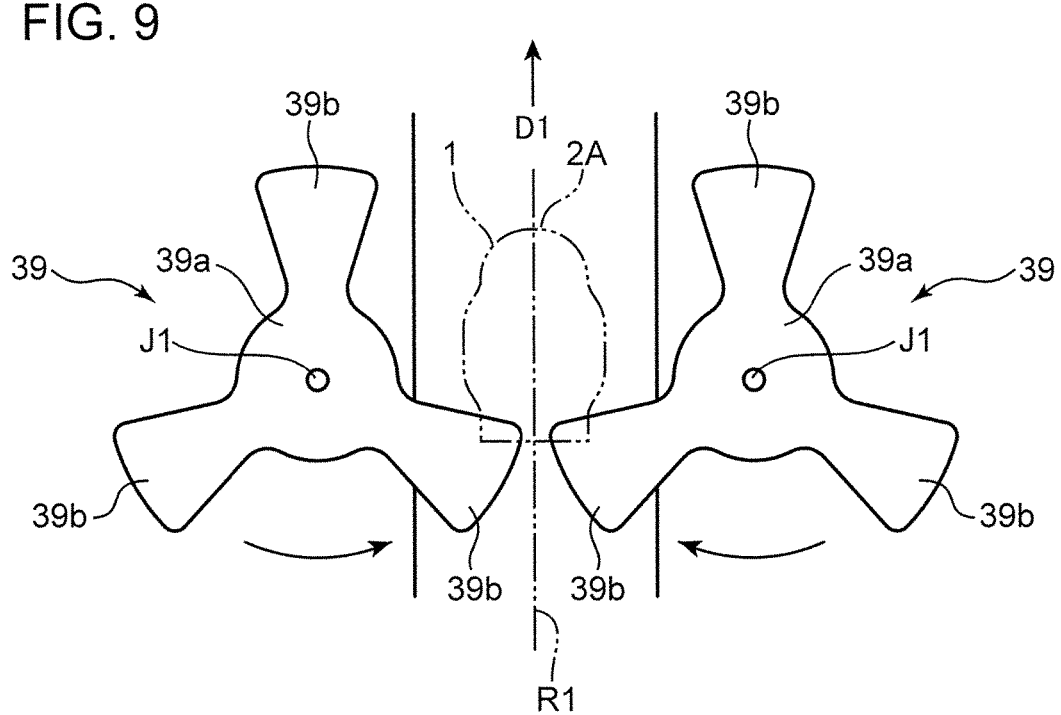
FIG. 9 is a plan view showing the operation of the folding device in FIG. 5 and shows a state in which the blades of impellers catch up with the disposable diaper.
Figure 10:
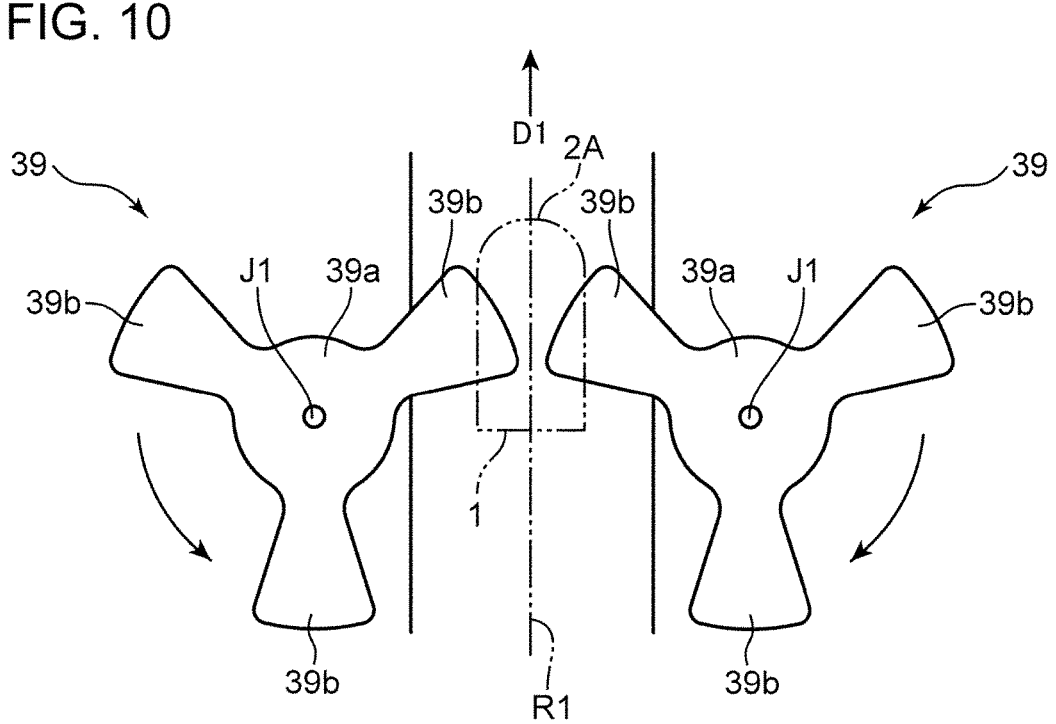
FIG. 10 is a plan view showing the operation of the folding device in FIG. 5 and shows a state just before the blades of the impellers pull ahead of the disposable diaper.

As shown in FIGS. 9 and 10, the folding motors 40 rotate the respective impellers 39 such that the blades 39b of the respective impellers 39 move from the upstream side to the downstream side on the conveying path R1 to be inserted between the front part and the rear part of the diaper main body 2. Note that the driving of the respective folding motors 40 is controlled by the controller 19 that will be described later such that the blades 39b of the respective impellers 39 synchronize with each other.

Hereinafter, a description will be given of the controller 19 with reference to FIGS. 5 to 10.

The controller 19 controls the driving of the first conveying unit 15 and the second conveying unit 16 such that the cycle of the restricted attracting regions 20c (see FIG. 6) of the first belt 20 and the cycle of the limited attracting regions 27c (see FIG. 8) of the second belt 27 coincide with each other. Specifically, based on the detection signals D1 and D2 from the first sensor 26 and the second sensor 33, the controller 19 feedback-controls the rates of the first conveying motor 24 and the second conveying motor 31 (outputs control signals S1 and S2) such that the cycle of the restricted attracting regions 20c and the cycle of the limited attracting regions 27c coincide with each other.

Here, the coincidence between the cycle of the restricted attracting regions 20c and the cycle of the limited attracting regions 27c represents the alignment between the restricted attracting regions 20c and the limited attracting regions 27c by which the positions of the ends of the restricted attracting regions 20c on the upstream side (right side in FIG. 6) and the positions of the ends of the limited attracting region 27c on the upstream side (right side in FIG. 8) coincide with each other. Thus, in a state in which the crease 2A of the disposable diaper 1 is directed to the downstream side of the conveying path R1, the diaper main body 2 can be attracted by the first belt 20 in nearly the entire region of the front part or the rear part thereof while the diaper main body 2 can be attracted by the second belt 27 in the range other than the non-attracting range E1 of the front part or the rear part thereof.

In addition, the controller 19 controls the rate of the third conveying motor 37 (outputs a control signal S3) such that the rate of the third belt 34 corresponds to the rates of the first belt 20 and the second belt 27. Thus, the front part or the rear part of the diaper main body 2 attracted by the second belt 27 can be smoothly transferred to the third belt 34, and the transferred disposable diaper 1 can be conveyed between the first belt 20 and the third belt 34.

Moreover, the controller 19 controls the rate of the folding motors 40 such that the rotating rate of the respective impellers 39 becomes higher than the conveying rate of the disposable diaper 1 with the movement of the first belt 20. Specifically, the controller 19 outputs, to the folding motor 40, a control signal S4 for rotating the impellers 39 at a rate higher than the rates of the first conveying motor 24 and the third conveying motor 37 set by the control described above. In the embodiment, the controller 19 controls the rate of the folding motor 40 such that the rotating rate of the impellers 39 become 107% as high as the conveying rate of the disposable diaper 1.

Thus, as shown in FIGS. 8 and 9, the controller 19 can rotate the blades 39b of the impellers 39 so as to pull ahead of the disposable diaper 1 conveyed by the first belt 20 and the third belt 34. Therefore, the blades 39b can be inserted between the front part and the rear part of the diaper main body 2 via the waist opening of the disposable diaper 1, and the respective side panels 3 and 4 can be folded inward between the front part and the rear part of the diaper main body 2 in such a way as to push out the diaper main body 2 from the inside of the crease 2A with the blades 39*b*.

Hereinafter, a description will be given, with reference to FIGS. 5 to 10, of a folding method for the disposable diaper 1 using the folding device 14.

The disposable diaper 1 is supplied to the folding device 14 from a step on the upstream side with the crease 2A directed to the downstream side. While holding this posture, the disposable diaper 1 is inserted between the first belt 20 and the second belt 27.

<Separating Step>

In the folding device 14, the front part of the diaper main body 2 is attracted by one of the first belt 20 and the second belt 27, and the rear part thereof is attracted by the other of the first belt 20 and the second belt 27.

In this state, the front part and the rear part of the diaper main body 2 are separated from each other while the disposable diaper 1 is conveyed along the conveying path R1 with the movement of both the belts 20 and 27. Specifically, as shown in FIG. 8, the diaper main body 2 is attracted by the second belt 27 only in the range other than the non-attracting range E1 thereof covering from the crease 2A to a predetermined position in the longitudinal direction. Therefore, when the diaper main body 2 is conveyed by both the belts 20 and 27, the front part and the rear part of the diaper main body 2 can be separated from each other while the diaper main body 2 is separated from the second belt 27 in the non-attracting range E1 thereof.

Note that in the separating step, the controller 19 controls the driving of the first conveying unit 15 and the second conveying unit 16 such that the cycle of the restricted attracting region 20*c* and the cycle of the limited attracting region 27*c* coincide with each other based on the position of the mark 20*d* of the first belt 20 and the position of the mark 27*d* of the second belt 27. Thus, the positioning between the diaper main body 2 and the restricted attracting region 20*c* and the limited attracting region 27*c* can accurately be performed.

<Approaching Step>

In an approaching step, the disposable diaper 1 conveyed by the first belt 20 and the second belt 27 in the separating step is conveyed by the first belt 20 and the third belt 34 while holding its posture. That is, the diaper main body 2 is transferred from the second belt 27 to the third belt 34 while the diaper main body 2 remains attracted by the first belt 20.

In this state, the front part and the rear part of the diaper main body 2 come close to each other while the disposable diaper 1 is conveyed along the conveying path R1 with the movement of the first belt 20 and the third belt 34.

<Folding Step>

A folding step according to the embodiment is performed during the period of the approaching step.

In the folding step, the respective impellers 39 are rotated such that the blades 39*b* of the respective impellers 39 move from the upstream side to the downstream side on the conveying path R1 to be inserted between the front part and the rear part of the diaper main body 2. Here, the rotating rate of the respective impellers 39 is set to be higher than the conveying rate of the disposable diaper 1 with the movement of the first belt 20. Thus, the respective side panels 3 and 4 can be folded inward between the front part and the rear part of the diaper main body 2 with the rotation of the respective impellers 39.

As described above, the diaper main body 2 is attracted by the first belt 20 and the second belt 27 only in the range other than the non-attracting range E1 thereof. In this way, the separation between the front part and the rear part of the diaper main body 2 can be allowed by an amount corresponding to the longitudinal size of the non-attracting range E1.

Accordingly, in order to obtain advantageous packaging, it becomes possible to separate the front part and the rear part of the diaper main body 2 from each other and reliably fold the respective side panel pieces 3 and 4 inward between the front part and the rear part of the diaper main body 2 while conveying the disposable diaper 1 with the crease 2A preceding.

Further, according to the embodiment, the following effects are produced.

According to the embodiment, since the disposable diaper 1 is conveyed by the first belt 20 and the third belt 34, the front part and the rear part of the diaper main body 2 can come close to each other in a state in which the respective side panel pieces 3 and 4 are folded inward between the front part and the rear part of the diaper main body 2. Therefore, the disposable diaper 1 can be conveyed to the next step (for example, a packaging step) in its folded state in which the thickness size is further reduced.

If the rotating rate of the impellers 39 is lower than the conveying rate of the disposable diaper 1 when the disposable diaper 1 is conveyed such that the crease 2A precedes as described above, the portion of the crease 2A of the disposable diaper 1 comes in contact with the blades 39*b* when the disposable diaper 1 pulls ahead of the blades 39*b*. As a result, it becomes difficult to reliably fold the respective side panel pieces 3 and 4. To this end, as shown in FIGS. 9 and 10, the rotating rate of the impellers 39 is set at a rate at which the blades 39*b* pull ahead of the disposable diaper 1. Thus, the blades 39*b* can be inserted between the front part and the rear part of the diaper main body 2 via the waist opening, and the respective side panel pieces 3 and 4 can be folded inward between the front part and the rear part of the diaper main body 2 in such a way as to push out the diaper main body 2 from the inside of the crease 2A with the blades 39*b*.

In the embodiment, each of the attracting regions (the restricted attracting regions 20*c* and the limited attracting regions 27*c*) of the first belt 20 and the second belt 27 is restricted in a range corresponding to the size of the front part or the rear part of one diaper main body 2. Since the regions for exerting an attracting force are restricted in this way, the attracting force in the respective attracting regions can be increased.

Further, the respective belts 20 and 27 move in a state in which the cycle of the restricted attracting regions 20*c* of the first belt 20 and the cycle of the limited attracting regions 27*c* of the second belt 27 coincide with each other. Therefore, in order to be capable of successively attracting a plurality of diaper main bodies 2, the first belt 20 and the second belt 27 can move in a state in which the restricted attracting regions 20*c* of the first belt 20 and the limited attracting regions 27*c* of the second belt 27 face each other.

Similarly to the above embodiment, in the case of the configuration in which the respective belts 20 and 27 slidingly contact the suctioning sections 25 and 32, respectively, to impart an attracting force to the respective attracting regions 20*c* and 27*c*, the sliding resistance between the respective belts 20 and 27 and the suctioning sections 25 and 32 increases with an increase in the attracting force accompanied by the restriction of the attracting regions 20*c* and 28*c* as described above. In this regard, if geared belts are employed as the respective belts 20 and 27 and joined to the respective motors 24 and 31 using gears, there is a problem in which the loads of the respective motors 24 and 31 and the gears increase and vibrations and noises are caused when the geared belts and rollers that support the geared belts interfere with each other.

Therefore, in the embodiment, the first belt 20 and the second belt 27 are formed by flat belts to which power is transmitted from the motors 24 and 31 without gears. Thus, since the relative movement between the motors 24 and 31, the rollers 21 to 23, the rollers 28 to 30, and the supporting rollers 44 and the respective belts 20 and 27 is allowed, the loads and the vibrations of the motors 24 and 31 and the noises thereof can be reduced.

Further, in the embodiment, the cycle of the restricted attracting regions 20c of the first belt 20 and the cycle of the limited attracting regions 27c of the second belt 27 coincide with each other based on the positions of the marks 20d and 27d of the respective belts 20 and 27. Thus, even if the relative movement between the motors 24 and 31 and the respective belts 20 and 27 is allowed as described above, the disposable diapers 1 can be reliably conveyed one by one with the cycle of the restricted attracting regions 20c of the first belt 20 and the cycle of the limited attracting regions 27c of the second belt 27 coinciding with each other.

Note that although the embodiment provides the restricted attracting regions 20c only in the first belt 20, they may also be provided in the second belt 27.

In addition, although the embodiment describes the folding unit 18 capable of folding the respective side panel pieces 3 and 4 inward between the front part and the rear part of the diaper main body 2 at the place between the first belt 20 and the third belt 34, the folding unit 18 can be one capable of folding the respective side panel pieces 3 and 4 inward between the front part and the rear part of the diaper main body 2 on the downstream side between the first belt 20 and the second belt 27, i.e., at a position after the front part and the rear part of the diaper main body 2 separate from each other.

Moreover, although the embodiment describes an example in which the first belt 20 and the second belt 27 are formed by flat belts, they may be formed by geared belts to which power is transmitted from the motors 24 and 31 via gears. In this case, since the cycle of the restricted attracting regions 20c of the first belt 20 and the cycle of the limited attracting regions 27c of the second belt 27 can mechanically coincide with each other, the feedback control of the controller 19 described above can be omitted.

Note that the specific embodiment described above mainly includes the inventions having the following configurations.

In order to solve the above problem, the inventors of the present application have employed a method for folding respective side portions inward between the front part and the rear part of a main body portion while conveying a disposable diaper with the crease of the main body portion directed to a downstream side. However, when the crease of the main body portion is directed to the downstream side, the front part and the rear part of the main body portion are constrained to each other by the crease on the distal end side thereof. Therefore, the front part and the rear part cannot be separated from each other only by holding the entire front part and the entire rear part of the main body portion with two conveying belts and separating the conveying belts from each other. To this end, the inventors of the present application have conceived the following inventions in which the position(s) of the front part and/or the rear part of a main body portion attracted by respective conveying belts is/are adjusted to allow the separation between the front part and the rear part of the main body portion with the crease of the main body portion directed to a downstream side.

Specifically, the present invention provides a disposable diaper folding method for a disposable diaper having a main body portion that extends from a front belly part to a back part via a crotch part of a wearer when the disposable diaper is worn and a pair of side portions that joins together a front part and a rear part of the main body portion folded in half based on a crease, the method comprising: a separating step of moving a first belt and a second belt in a state in which the front part of the main body portion is attracted by one of the first belt and the second belt and the rear part of the main body portion is attracted by the other of the first belt and the second belt, and separating the front part and the rear part of the main body portion from each other while conveying the disposable diaper along a predetermined conveying path by a movement of the first and the second belt, the first belt and the second belt being arranged so as to face each other across the conveying path for the disposable diaper and separate from each other as the first belt and the second belt move to a downstream side of the conveying path; and a folding step of folding the respective side portions inward between the front part and the rear part of the main body portion, which are separated from each other, wherein the separating step conveys the disposable diaper along the conveying path such that the crease is directed to the downstream side in a state in which the main body portion is attracted by at least one of the first belt and the second belt only in a range other than a non-attracting range thereof covering from the crease to a predetermined position in a longitudinal direction, thereby separating the front part and the rear part of the main body portion from each other while separating the main body portion from at least the one belt in the non-attracting range.

In addition, the present invention provides a disposable diaper folding device for a disposable diaper having a main body portion that extends from a front belly part to a back part via a crotch part of a wearer when the disposable diaper is worn and a pair of side portions that joins together a front part and a rear part of the main body portion folded in half based on a crease, the device comprising: a first conveying unit that has a first belt and a first moving mechanism configured to move the first belt in a state in which one of the front part and the rear part of the main body portion is attracted by the first belt; a second conveying unit that has a second belt arranged so as to face the first belt across a predetermined conveying path and separate from the first belt as the second belt moves to a downstream side of the conveying path and that has a second moving mechanism configured to move the second belt in a state in which the other of the front part and the rear part of the main body portion is attracted by the second belt such that the front part and the rear part of the main body portion separate from each other while conveying the disposable diaper along the conveying path in cooperation with the first belt; and a folding unit that folds the respective side portions inward between the front part and the rear part of the main body portion, the front part and the rear part being separated from each other by the first conveying unit and the second conveying unit, wherein at least one of the first belt and the second belt has a plurality of limited attracting regions for attracting the main body portion only in a range other than a non-attracting range thereof covering from the crease to a predetermined position in a longitudinal direction, and the first conveying unit and the second conveying unit convey the disposable diaper along the conveying path such that the crease is directed to the downstream side in a state in which the main body portion is attracted to the limited attracting region only in the range other than the non-attracting range thereof, thereby separating the front part and the rear part of the main body portion from each other while separating the main body portion from at least the one belt in the non-attracting range.

According to these inventions, the main body portion is attracted by the first belt and the second belt only in the range other than the non-attracting range thereof. In this way, the separation between the front part and the rear part of the main body portion can be allowed by an amount corresponding to the longitudinal size of the non-attracting range.

Hence, according to each of the inventions, it becomes possible to separate the front part and the rear part of the main body portion from each other and reliably fold the respective side portions inward between the front part and the rear part of the main body portion while conveying the disposable diaper with the crease preceding in order to obtain advantageous packaging.

The folding method preferably further comprises an approaching step of moving the first belt and a third belt in a state in which the front part or the rear part of the main body portion transferred from the second belt is attracted by the third belt to cause the front part and the rear part of the main body portion come close to each other while conveying the disposable diaper along the conveying path, the third belt being arranged so as to face an extended portion of the first belt across the conveying path and come close to the first belt as the third belt moves to the downstream side of the conveying path, and the extended portion extending to the downstream side of the second belt on the conveying path, wherein the folding step is preferably performed after the front part and the rear part of the main body portion are separated from each other in the separating step or during a period of implementing the approaching step.

In addition, the folding device preferably further comprises a third conveying unit that has a third belt configured to receive the front part or the rear part of the main body portion attracted by the second belt and arranged so as to face an extended portion of the first belt, which extends to the downstream side of the second belt on the conveying path, across the conveying path and come close to the first belt as the third belt moves to the downstream side of the conveying path and that has a third moving mechanism configured to move the third belt in a state in which the front part or the rear part of the main body portion is attracted by the third belt such that the front part and the rear part of the main body portion come close to each other while conveying the disposable diaper along the conveying path in cooperation with the first belt, wherein the folding unit is preferably configured to fold the respective side portions inward between the front part and the rear part of the main body portion on the downstream side between the first belt and the second belt or between the first belt and the third belt.

According to these aspects, since the disposable diaper is conveyed by the first belt and the third belt, the front part and the rear part of the main body portion can come close to each other in a state in which the respective side portions are folded inward between the front part and the rear part of the main body portion. Therefore, the disposable diaper can be conveyed to the next step (for example, a packaging step) in its folded state in which the thickness size is further reduced.

In the folding method, the folding step preferably rotates a pair of impellers, which is provided on both sides of the first belt across the conveying path and has blades, so as to move the blades from an upstream side to the downstream side on the conveying path and to be inserted between the front part and the rear part of the main body portion, and a rotating rate of each of the impellers is preferably higher than a conveying rate of the disposable diaper with the movement of the first belt.

In addition, in the folding device, the folding unit preferably has a pair of impellers that is provided on both sides of the first belt across the conveying path and has blades and a pair of folding driving sections that is configured to rotate the respective impellers so as to move the blades from an upstream side to the downstream side on the conveying path to be inserted between the front part and the rear part of the main body portion, and a rotating rate of the respective impellers is preferably set to be higher than a conveying rate of the disposable diaper with the movement of the first belt.

If the rotating rate of the impellers is lower than the conveying rate of the disposable diaper when the disposable diaper is conveyed such that the crease precedes as described above, the portion of the crease of the disposable diaper comes in contact with the blades when the disposable diaper pulls ahead of the blades. As a result, it becomes difficult to reliably fold the respective side portions. To this end, as described in the respective aspects, the rotating rate of the impellers is set at a rate at which the blades pull ahead of the disposable diaper. Thus, the blades can be inserted between the front part and the rear part of the main body portion via the waist opening, and the respective side portions can be folded inward between the front part and the rear part of the main body portion in such a way as to push out the main body portion from the inside of the crease with the blades.

In the folding method, each of the first belt and the second belt preferably has a plurality of attracting regions, each of which is restricted in a range corresponding to a size of the front part or the rear part of the one main body portion, and the separating step preferably moves both the belts such that a cycle of the attracting regions of the first belt and a cycle of the attracting regions of the second belt coincide with each other.

In the folding device, the belt other than the belt having the limited attracting regions among the first belt and the second belt preferably has a plurality of restricted attracting regions, each of the plurality of restricted attracting regions and the plurality of limited attracting regions being restricted in a range corresponding to a size of the front part or the rear part of the one main body portion, and the first belt and the second belt preferably move in a state in which the cycle of the limited attracting regions and the cycle of the restricted attracting regions coincide with each other.

In these aspects, each of the attracting regions of the first belt and the second belt is restricted to the range corresponding to the size of the front part or the rear part of the main body portion. Since the regions for exerting an attracting force are restricted in this way, the attracting force in the respective attracting regions can be increased.

Further, the respective belts move in a state in which the cycle of the attracting regions of the first belt and the cycle of the attracting regions of the second belt coincide with each other. Therefore, in order to be capable of successively attracting a plurality of main body portions, the first belt and the second belt can move in a state in which the attracting regions of the first belt and the attracting regions of the second belt face each other.

In the folding method, each of the first belt and the second belt is preferably formed by a flat belt and has a plurality of marks that indicate positions of the respective attracting regions, and the separating step preferably causes a first suctioning section, which has a first suctioning chamber set at negative pressure, slidingly contact the first belt such that each of the suctioning regions successively face the first suctioning chamber and causes a second suctioning section, which has a second suctioning chamber set at negative pressure, slidingly contact the second belt such that the respective attracting regions successively face the second suctioning chamber, thereby imparting an attracting force to the respective attracting regions and making the cycle of the attracting regions of the first belt and the cycle of the attracting regions of the second belt coincide with each other based on the positions of the marks.

In addition, in the folding device, each of the first belt and the second belt is preferably formed by a flat belt and has a plurality of marks that indicate positions of the respective limited attracting regions or the respective restricted attracting regions, the first moving mechanism preferably has a first suctioning section that has a first suctioning chamber set at negative pressure and slidingly contacts the first belt such that the respective limited attracting regions or the respective restricted attracting regions successively face the first suctioning chamber, and has a first detector that detects the marks of the first belt, the second moving mechanism preferably has a second suctioning section that has a second suctioning chamber set at negative pressure and slidingly contacts the second belt such that the respective limited attracting regions or the respective restricted attracting regions successively face the second suctioning chamber, and has a second detector that detects the marks of the second belt, and the disposable diaper folding device preferably further comprises a controller that controls driving of the first moving mechanism and the second moving mechanism such that the cycle of the limited attracting regions and the cycle of the restricted attracting regions coincide with each other based on detection results of the marks.

In the case of the configuration in which the respective belts slidingly contact the suctioning sections to impart an attracting force to the respective attracting regions as in the respective aspects, the sliding resistance between the respective belts and the suctioning sections increases with an increase in the attracting force accompanied by the restriction of the attracting regions as described above. In this regard, if geared belts are employed as the respective belts and joined to the driving sources (motors or the like) using gears, there is a problem in which the loads of the driving sources and the gears increase and vibrations and noises are caused when the geared belts and rollers that support the geared belts interfere with each other.

Therefore, in the respective aspects, the first belt and the second belt are formed by flat belts to which power is transmitted from the driving sources without gears. Thus, since the relative movement between the driving sources, the rollers, and the respective belts is allowed, the loads of the driving sources and the vibrations and the noises can be reduced.

Further, in the respective aspects, the cycle of the attracting regions of the first belt and the cycle of the attracting regions of the second belt coincide with each other based on the positions of the marks of the respective belts. Thus, even if the relative movement between the driving sources and the respective belts is allowed as described above, the disposable diapers can be reliably conveyed one by one with the cycle of the attracting regions of the first belt and the cycle of the attracting regions of the second belt coinciding with each other.

The invention claimed is:

1. A disposable diaper folding method for a disposable diaper having a main body portion that extends from a front belly part to a back part via a crotch part of a wearer when the disposable diaper is worn and a pair of side portions that joins together a front part and a rear part of the main body portion folded in half based on a crease, the method comprising:

a separating step of moving a first belt and a second belt in a state in which the front part of the main body portion is attracted by one of the first belt and the second belt and the rear part of the main body portion is attracted by the other of the first belt and the second belt and separating the front part and the rear part of the main body portion from each other while conveying the disposable diaper along a predetermined conveying path by a movement of the first belt and the second belt, the first belt and the second belt being arranged so as to face each other across the conveying path for the disposable diaper and separate from each other as the first belt and the second belt move to a downstream side of the conveying path; and a folding step of folding the respective side portions inward between the front part and the rear part of the main body portion, which are separated from each other, wherein the separating step conveys the disposable diaper along the conveying path such that the crease precedes a portion of the main body portion other than the crease in a state in which the main body portion is attracted by at least one of the first belt and the second belt only in a range other than a non-attracting range thereof covering from the crease to a predetermined position in a longitudinal direction along the conveying path, thereby separating the front part and the rear part of the main body portion from each other while separating the main body portion from the at least one of the first and second belt in the non-attracting range, each of the first belt and the second belt has a plurality of attracting regions, each of which is restricted in a range corresponding to a size of the front part or the rear part of the one main body portion in the longitudinal direction along the conveying path and is provided so as to be spaced apart from each other in the longitudinal direction along the conveying path, and the separating step moves both of the belts such that a cycle of the attracting regions of the first belt and a cycle of the attracting regions of the second belt coincide with each other.

2. The disposable diaper folding method according to claim 1, further comprising:

an approaching step of moving the first belt and a third belt in a state in which the front part or the rear part of the main body portion transferred from the second belt is attracted by the third belt to cause the front part and the rear part of the main body portion to come close to each other while conveying the disposable diaper along the conveying path, the third belt being arranged so as to face an extended portion of the first belt across the conveying path and come close to the first belt as the third belt moves to the downstream side of the conveying path, and the extended portion extending to the downstream side of the second belt on the conveying path, wherein the folding step is performed after the front part and the rear part of the main body portion are separated from each other in the separating step or during a period of implementing the approaching step.

3. The disposable diaper folding method according to claim 2, wherein the folding step rotates a pair of impellers, which is provided on both sides of the first belt across the conveying path and has blades, so as to move the blades from an upstream side to the downstream side on the conveying path and to be inserted between the front part and the rear part of the main body portion, and a rotating rate of each of the impellers is higher than a conveying rate of the disposable diaper with the movement of the first belt.

4. The disposable diaper folding method according to claim 1, wherein each of the first belt and the second belt is formed by a flat belt and has a plurality of marks that indicate positions of the respective attracting regions, and the separating step causes a first suctioning section, which has a first suctioning chamber set at negative pressure, slidingly contact the first belt such that the respective suctioning regions successively face the first suctioning chamber and causes a second suctioning section, which has a second suctioning chamber set at negative pressure, slidingly contact the second belt such that the respective attracting regions successively face the second suctioning chamber, thereby imparting an attracting force to each of the attracting regions and making the cycle of the attracting regions of the first belt and the cycle of the attracting regions of the second belt coincide with each other based on the positions of the marks.

5. The disposable diaper folding method according to claim 1, wherein the separating step conveys the disposable diaper along the conveying path such that the crease is directed toward the downstream side along the conveying path.

6. The disposable diaper folding method according to claim 1, wherein the separating step conveys the disposable diaper along the conveying path such that the crease precedes all portions of the main body portion other than the crease.

7. A disposable diaper folding device for a disposable diaper having a main body portion that extends from a front belly part to a back part via a crotch part of a wearer when the disposable diaper is worn and a pair of side portions that joins together a front part and a rear part of the main body portion folded in half based on a crease, the device comprising:

a first conveying unit that has a first belt and a first moving mechanism configured to move the first belt in a state in which one of the front part and the rear part of the main body portion is attracted by the first belt;

a second conveying unit that has a second belt arranged so as to face the first belt across a predetermined conveying path and separate from the first belt as the second belt moves to a downstream side of the conveying path and that has a second moving mechanism configured to move the second belt in a state in which the other of the front part and the rear part of the main body portion is attracted by the second belt such that the front part and the rear part of the main body portion separate from each other while conveying the disposable diaper along the conveying path in cooperation with the first belt;

a folding unit that folds the respective side portions inward between the front part and the rear part of the main body portion, the front part and the rear part being separated from each other by the first conveying unit and the second conveying unit, wherein at least one of the first belt and the second belt has a plurality of limited attracting regions for attracting the main body portion only in a range other than a non-attracting range thereof covering from the crease to a predetermined position in a longitudinal direction along the conveying path, and the first conveying unit and the second conveying unit convey the disposable diaper along the conveying path such that the crease precedes a portion of the main body portion other than the crease in a state in which the main body portion is attracted to the limited attracting region only in the range other than the non-attracting range thereof, thereby separating the front part and the rear part of the main body portion from each other while separating the main body portion from the at least one of the first and second belt in the non-attracting range, the belt other than the belt having the limited attracting regions among the first belt and the second belt has a plurality of restricted attracting regions, each of the plurality of restricted attracting regions and the plurality of limited attracting regions being restricted in a range corresponding to a size of the front part or the rear part of the one main body portion in the longitudinal direction along the conveying path and being provided so as to be spaced apart from each other in the longitudinal direction along the conveying path, and the first belt and the second belt move in a state in which the cycle of the limited attracting regions and the cycle of the restricted attracting regions coincide with each other.

8. The disposable diaper folding device according to claim 7, further comprising:

a third conveying unit that has a third belt configured to receive the front part or the rear part of the main body portion attracted by the second belt and arranged so as to face an extended portion of the first belt, which extends to the downstream side of the second belt on the conveying path, across the conveying path and come close to the first belt as the third belt moves to the downstream side of the conveying path and that has a third moving mechanism configured to move the third belt in a state in which the front part or the rear part of the main body portion is attracted by the third belt such that the front part and the rear part of the main body portion come close to each other while conveying the disposable diaper along the conveying path in cooperation with the first belt, wherein the folding unit is configured to fold the respective side portions inward between the front part and the rear part of the main body portion on the downstream side between the first belt and the second belt or between the first belt and the third belt.

9. The disposable diaper folding device according to claim 8, wherein the folding unit has a pair of impellers that is provided on both sides of the first belt across the conveying path and has blades, and a pair of folding driving sections that is configured to rotate the respective impellers so as to move the blades from an upstream side to the downstream side on the conveying path and to be inserted between the front part and the rear part of the main body portion, and a rotating rate of each of the impellers is set to be higher than a conveying rate of the disposable diaper with the movement of the first belt.

10. The disposable diaper folding device according to claim 7, wherein each of the first belt and the second belt is formed by a flat belt and has a plurality of marks that indicate positions of the respective limited attracting regions or the respective restricted attracting regions, the first moving mechanism has a first suctioning section that has a first suctioning chamber set at negative pressure and slidingly contacts the first belt such that the respective limited attracting regions or the respective restricted attracting regions successively face the first suctioning chamber, and has a first detector that detects the marks of the first belt, the second moving mechanism has a second suctioning section that has a second suctioning chamber set at negative pressure and slidingly contacts the second belt such that the respective limited attracting regions or the respective restricted attracting regions successively face the second suctioning chamber, and has a second detector that detects the marks of the second belt, and the disposable diaper folding device further comprises a controller that controls driving of the first moving mechanism and the second moving mechanism such that the cycle of the limited attracting regions and the cycle of the restricted attracting regions coincide with each other based on detection results of the marks.

11. The disposable diaper folding device according to claim 7, wherein the first conveying unit and the second conveying unit convey the disposable diaper along the conveying path such that the crease is directed toward the downstream side along the conveying path.

12. The disposable diaper folding device according to claim 7, wherein the first conveying unit and the second conveying unit convey the disposable diaper along the conveying path such that the crease precedes all portions of the main body portion other than the crease.

\* \* \* \* \*